(12) United States Patent
Pierce et al.

(10) Patent No.: US 9,011,281 B2
(45) Date of Patent: Apr. 21, 2015

(54) AMMUNITION DELIVERY SYSTEM ARROWHEAD AND METHOD OF USE

(71) Applicant: Rac Em Bac, L.L.C., DeQuincy, LA (US)

(72) Inventors: William Fred Pierce, DeQuincy, LA (US); Tony James Latiolais, DeQuincy, LA (US)

(73) Assignee: Rac Em Bac, L.L.C., DeQuincy, LA (US)

( * ) Notice: Subject to any disclaimer, the term of this patent is extended or adjusted under 35 U.S.C. 154(b) by 95 days.

(21) Appl. No.: 13/764,302

(22) Filed: Feb. 11, 2013

(65) Prior Publication Data

US 2013/0205633 A1    Aug. 15, 2013

Related U.S. Application Data

(63) Continuation-in-part of application No. 13/726,446, filed on Dec. 24, 2012, and a continuation-in-part of application No. 13/488,684, filed on Jun. 5, 2012, now Pat. No. 8,568,257, which is a continuation-in-part of application No. 13/199,901, filed on Sep. 13, 2011, now Pat. No. 8,444,512, which is a continuation-in-part of application No. 12/928,772, filed on Dec. 16, 2010, now Pat. No. 8,439,777.

(60) Provisional application No. 61/649,816, filed on May 21, 2012.

(51) Int. Cl.
| | | |
|---|---|---|
| *F42B 6/08* | (2006.01) | |
| *F41A 19/25* | (2006.01) | |
| *A61L 9/12* | (2006.01) | |
| *F42B 12/36* | (2006.01) | |

(52) U.S. Cl.
CPC . *F41A 19/25* (2013.01); *A61L 9/12* (2013.01); *F42B 6/08* (2013.01); *F42B 12/362* (2013.01)

(58) Field of Classification Search
USPC .......................................... 473/578, 582, 583
See application file for complete search history.

(56) References Cited

U.S. PATENT DOCUMENTS

| | | | | |
|---|---|---|---|---|
| 3,580,172 | A * | 5/1971 | Hendricks | 102/371 |
| 3,747,247 | A * | 7/1973 | McNair | 42/1.14 |
| 4,762,328 | A * | 8/1988 | Beyl | 473/585 |
| 6,311,623 | B1 * | 11/2001 | Zaruba | 102/371 |
| 6,439,127 | B1 | 8/2002 | Cherry | |

* cited by examiner

*Primary Examiner* — John Ricci
(74) *Attorney, Agent, or Firm* — Schultz & Associates, P.C.

(57) ABSTRACT

A device and method introduces the use of conventional ammunitions to the archery/bow hunting industry. The device achieves stealthy delivery of firearm munitions and increases the firepower of standard arrows resulting in deeper penetration into a target. The device consists generally of a cylindrical housing threaded internally on one end for attachment to a firing pin. A cartridge is loaded into the housing until the flange on the cartridge casing abuts an interior shoulder. In an alternate embodiment, the interior of the housing further includes an annular retaining tab. The retaining tab separates the cartridge from the firing pin to prevent inadvertent discharge. A cap or nosecone may be included to further protect the device from accidental discharge of the cartridge and to provide aerodynamic advantages. The housing may further include a set of stabilizing vanes.

19 Claims, 8 Drawing Sheets

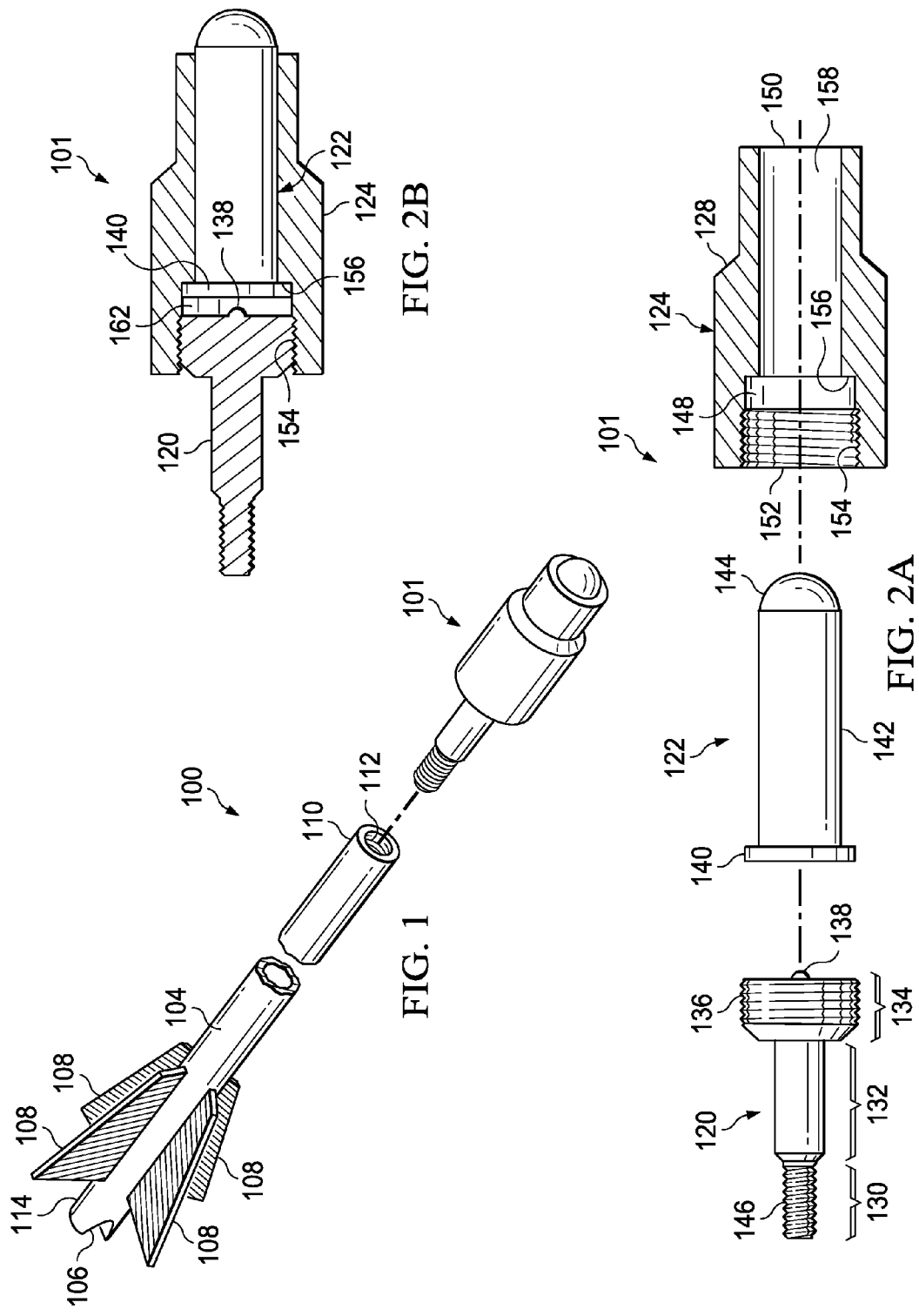

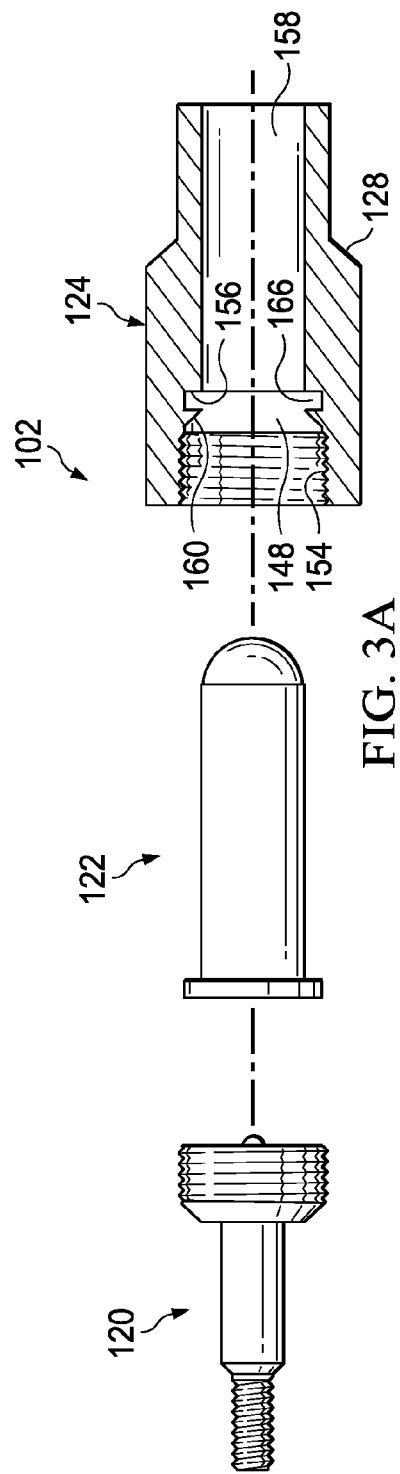
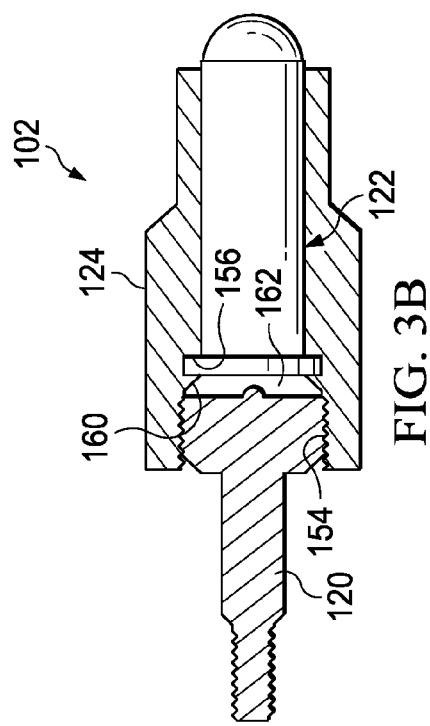
FIG. 3A
FIG. 3B

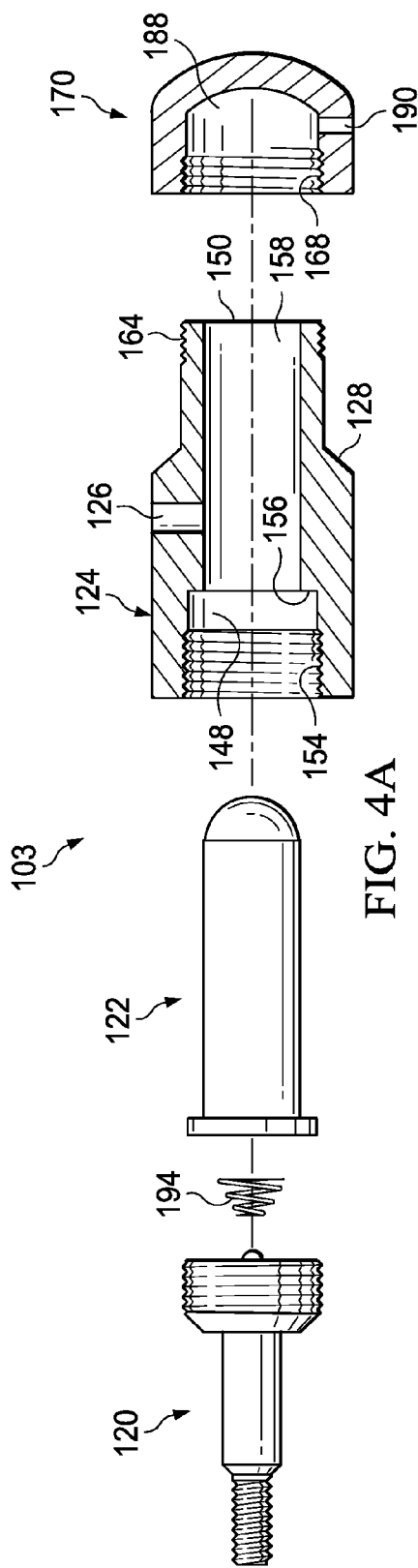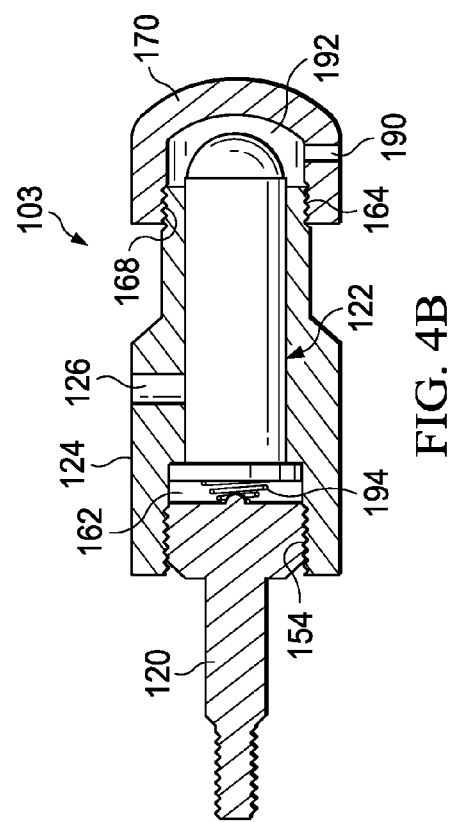

AMMUNITION DELIVERY SYSTEM ARROWHEAD AND METHOD OF USE

CROSS-REFERENCE TO RELATED APPLICATIONS

This application is a Continuation-In-Part application claiming priority benefit from U.S. patent application Ser. No. 13/726,446 filed Dec. 24, 2012 which claims benefit from U.S. Provisional Patent Application No. 61/649,816 filed May 21, 2012 and from U.S. patent application Ser. No. 13/488,684 filed Jun. 5, 2012 which claims benefit from U.S. patent application Ser. No. 13/199,901 filed Sep. 13, 2011 which claims benefit from U.S. patent application Ser. No. 12/928,772 filed on Dec. 16, 2010.

FIELD OF INVENTION

This disclosure relates to hunting equipment, and more particularly to an arrowhead capable of delivering firearm munitions stealthily and accurately to a target.

BACKGROUND OF THE INVENTION

In the sport of game hunting, the element of surprise is a valuable asset in the hunter's arsenal. If an intended game target is unaware that a hunter is near, the hunter's chances of landing the game are increased. Several methods of hiding a hunter are typically employed such as camouflage attire, hidden game blinds, and scent dispersing apparatus to not only hide the scent of the hunter, but to attract the game. Additionally, hunters may choose to use bow and arrows or crossbows as their weapon of choice to avoid the loud, animal deterring sound of gunfire. The drawback of using a bow and arrow though is that the hunter typically needs to be closer to the intended target and the power that an arrow delivers to a target tends to be less than a typical firearm. A clean, accurate, and powerful strike to the intended game target resulting in quick drop and expiration is most desirable.

The novel device and method discussed herein allows for the use of a bow and arrow or crossbow and delivers more power, energy, and accuracy to the archery industry than typical arrowheads. The device provides increased firepower, safety, accurate flight, clean deployment from the bow or crossbow, stealthy flight, and deeper penetration than standard arrowheads resulting in on the spot game expiration. Specifically, the device incorporates a standard bullet casing housed in a containment unit and paired with a firing pin that discharges the bullet only upon contact with the intended target.

U.S. Pat. No. 6,311,623 to Zaruba discloses an arrowhead having a powder-charged projectile activated after a delayed interval. The device includes a bullet-shaped arrowhead housing, with or without a protective tip, having a cartridge contained in a cavity within. A plunger extending from the housing has a protrusion for contact with the cartridge upon impact with a target. The plunger is threaded onto an arrow shaft. In use, the arrow shaft collides with the target. The momentum of the arrow causes the protrusion of the plunger to contact the cartridge which ignites a primer to fire the projectile.

U.S. Pat. No. 3,580,172 to Hendricks discloses an underwater projectile for firing a cartridge upon impact with a target. The projectile includes a tubular body having an open fore end portion defining a gun bore and an intermediate portion defining a chamber for receiving a cartridge. A firing pin is slidably disposed within the intermediate portion of the tubular body and engages the primer of the cartridge to detonate the cartridge and the slug.

U.S. Pat. No. 2,780,860 to Arpin discloses a power spear. The device comprises a barrel which is threaded onto a shaft. The barrel includes a cartridge chamber which has a shoulder for seating a rearward facing cartridge blank. The barrel further includes an open end which houses a projectile or spearhead. The projectile has a pointed striking head on one end and a projection extending from a flat end opposite the pointed head. In use, the device contacts a target which drives the projectile rearward. The projection strikes the primer of the cartridge as to detonate it. The cartridge case itself acts directly against the flat end of the projectile and expels the projectile from the barrel.

U.S. Pat. No. 2,620,190 to Bean discloses a cap for darts and arrows. The cap is frictionally engaged with the arrowhead and shaft of an arrow. The cap is tubular in shape and conceals the leading edge of a cartridge to prevent accidental discharge. Upon impact, the momentum of the arrow detonates the cartridge.

Therefore, there is a need in the art to combine the power of firearm munitions with the stealthy delivery of an arrow which provides increased firepower, safety, accurate flight, clean deployment from the bow or crossbow, stealthy flight, and deeper penetration than standard arrowheads resulting in an increased chance of on the spot game expiration.

SUMMARY OF INVENTION

The device disclosed combines advantages of conventional firearms ammunition with those of archery and bow hunting. The device delivers more power, energy, and accuracy to the archery industry than typical arrowheads. The device provides increased firepower, safety, accurate flight, clean deployment from the bow or crossbow, stealthy flight, and deeper penetration than standard arrowheads.

Accordingly, the device is comprised of a generally hollow cylindrical containment housing in which a single standard firearm round is seated. A firing pin is secured to one end of the containment housing. The round or cartridge is comprised of a brass casing and slug as is common in the art. The generally cylindrical firing pin is threaded on both a narrow end for engagement with an arrow shaft and a wider end for engagement with the containment housing. The firing pin comprises an axially aligned protrusion for use with centerfire cartridges or offset protrusions for use with rimfire cartridges. In an alternate embodiment, the firing pin can be spring loaded.

The containment housing is generally a tapered, hollow cylinder typically bored to accommodate .38 caliber, .357 caliber, or .22 caliber bullets. Other calibers can be accommodated. The containment housing is threaded internally on an end for attachment to the firing pin and further includes an interior shoulder separating two cavities. A cartridge is loaded into the containment housing until the flange on the casing abuts the shoulder. In an alternate embodiment, the interior of the containment housing further includes an annular retainer tab integrally formed in the interior of the housing containment. The retainer tab separates the cartridge from the firing pin to prevent inadvertent discharge. In an alternate embodiment, the exterior of the containment housing comprises a set of vanes.

In an alternate embodiment, the containment housing is threaded externally on an end opposite the firing pin for attachment of a safety cap. The safety cap is generally cylindrical in shape, includes an aerodynamically shaped nose, and further includes internal threads for attachment with the external threads of the containment housing. The safety cap protects the cartridge from accidental discharge and is typically not removed until the time of deployment of the weapon. An alternate embodiment includes a "ratcheting" feature that prevents the safety cap from removal after installation. An additional alternate embodiment discloses a safety cap frictionally engaged with the containment housing intended to remain engaged with the housing during use.

In use, a cartridge is loaded in the containment housing. In some embodiments the cap is attached to the tapered end of the containment housing. The firing pin is attached to the containment housing. The device is threaded onto an arrow shaft or bolt. The device, attached to an arrow shaft or bolt, is deployed at a target. Upon impact, the cartridge is driven back into the firing pin. The firing pin contacts the primer of the cartridge causing discharge. The slug is propelled into the target.

The result of use of the device is generally deeper penetration and quiet use of ammunition. A less powerful and lighter bow may be used in conjunction with the device and still achieve a more powerful strike than a standard arrowhead.

BRIEF DESCRIPTION OF DRAWINGS

Reference will now be made to the drawings, wherein like parts are designated by like numerals, and wherein:

FIG. 1 is an exploded perspective view of an ammunition delivery system arrowhead and arrow of this disclosure.

FIG. 2A is an exploded, partial cut-away view of an ammunition delivery system arrowhead of this disclosure.

FIG. 2B is an assembled, partial cut-away view of an ammunition delivery system arrowhead of this disclosure.

FIG. 3A is an exploded, partial cut-away view of an alternate embodiment of an ammunition delivery system arrowhead of this disclosure.

FIG. 3B is an assembled, partial cut-away view of an alternate embodiment of an ammunition delivery system arrowhead of this disclosure.

FIG. 4A is an exploded, partial cut-away view of an alternate embodiment of an ammunition delivery system arrowhead of this disclosure.

FIG. 4B is an assembled partial cut-away view of an alternate embodiment of an ammunition delivery system arrowhead of this disclosure.

DETAILED DESCRIPTION OF PREFERRED EMBODIMENTS

Figure 5A:
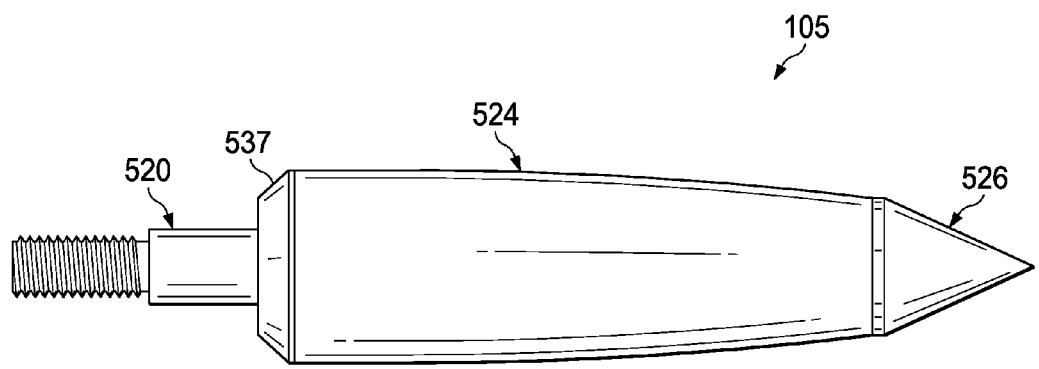
FIG. 5A is an elevation view of an alternate embodiment of an ammunition delivery system arrowhead of this disclosure.

In the descriptions that follow, like parts are marked throughout the specification and drawings with the same numerals, respectively. The drawing figures are not necessarily drawn to scale and certain figures may be shown in exaggerated or generalized form in the interest of clarity and conciseness.

Referring to FIG. 1, arrow 100 is comprised of shaft 104 attached to arrowhead 101. Shaft 104 has an open forward end 110 that includes internal threads 112. Nock 106 is formed in distant end 114 to accommodate a bow string. Forward end 110 of shaft 104 is open and arrowhead 101 is positioned therein. Fletchings 108 surround the circumference of shaft 104 equidistantly at distant end 114 adjacent nock 106. As is common in the art, two, three, or four fletchings may be incorporated.

FIGS. 2A and 2B show ammunition delivery system arrowhead 101. Arrowhead 101 is comprised of firing pin 120 threadably engaged with containment housing 124. Containment housing 124 is generally cylindrical and encases cartridge 122.

Firing pin 120 is comprised of threaded section 130, middle section 132, and head section 134. Threaded section 130 includes threads 146 sized to engage threads 112 of shaft 104. Threaded section 130 is integrally formed with middle section 132. Middle section 132 is cylindrically shaped and typically has a diameter generally equal to the diameter of shaft 104. Head section 134 is integrally formed with middle section 132 and further includes threads 136. Protrusion 138 extends from head section 134. Protrusion 138 is generally concentrically aligned with the longitudinal axis of firing pin 120 to operate with a centerfire cartridge but could also be offset in order to operate with a rimfire cartridge. Firing pin 120 is preferably manufactured of aluminum, steel, or rigid molded plastic.

Cartridge 122 is of design and composition common in the art. Cartridge 122 is comprised of casing 142 having base 140. Slug 144 is housed in and extends from casing 144. Cartridge 122 is preferably sized as .38 caliber, .357 caliber, or .22 caliber. However, containment housing 124 can be sized to accommodate any commercially available cartridge caliber as larger and smaller munitions are envisioned by this disclosure. Cartridge 122 may be a centerfire cartridge or a rimfire cartridge. Rimfire cartridges are typically limited to low pressure calibers because they require a thin casing so that a firing pin can crush the base and ignite the primer. Rimfire cartridges are relatively light and inexpensive as compared to centerfire cartridges.

Containment housing 124 is generally a hollow cylinder having rearward opening 152 and forward opening 150. The exterior of containment housing 124 has a leading end separated from a trailing end by collar ring 128. The diameter of the leading end is generally less than the diameter of the trailing end thus collar ring 128 provides aerodynamic advantages to help stabilize the arrowhead during use. The interior of containment housing 124 includes a cylindrically shaped cavity 158 adjacent a second concentrically aligned and cylindrically shaped cavity 148. Shoulder 156 separates cavity 148 from cavity 158. Rearward opening 152 is sized to accommodate head section 134 of firing pin 120. Rearward opening 152 leads to cavity 148. Cavity 148 includes threads 154 which engage threads 136. Forward opening 150 leads to cavity 158. Cavity 158 and forward opening 150 have a diameter only slightly larger than the diameter of casing 142 which allows cartridge 122 to be press fit inside containment housing 124 and frictionally held in place. In an alternate embodiment, an adhesive or induction welding may be employed to further secure cartridge 122 inside containment housing 124.

Containment housing 124 is preferably manufactured of molded plastic. In one embodiment, the plastic is an acrylic resin which is transparent to allow the cartridge to be seen through the housing in order to determine if the weapon is loaded. In another embodiment, the plastic is a low cost variety of polypropylene.

FIG. 2B shows arrowhead 101 as assembled. Cartridge 122 rests in cavity 158 and base 140 abuts shoulder 156. Slug 144 extends through forward opening 150. Head section 134 of firing pin 120 is threadably engaged with containment housing 124. Threads 154 and threads 136 prevent firing pin 120 from advancing too far into cavity 148. As a result, gap 162 exists between protrusion 138 and base 140. Threads 146 of threaded section 130 engage internal threads 112 to securely attach the arrowhead to shaft 104.

In use, cartridge 122 is loaded, slug 144 first, into containment housing 124 through rearward opening 152. Cartridge 122 is advanced through cavity 148 and through cavity 158 until base 140 abuts shoulder 156. Firing pin 120 is attached to containment housing 124 such that threads 136 engage threads 154. Firing pin 120 is tightened to containment housing 124 such that gap 162 exists between protrusion 138 and cartridge 122 to complete assembly of the ammunition delivery system arrowhead. Arrowhead 101 is attached to shaft 104 such that threads 146 engage internal threads 112 to complete assembly of arrow 100.

Arrow 100 is typically delivered to an intended target through the use of a bow or cross bow. When arrowhead 101 strikes the intended target, cartridge 122 slides backwards through containment housing 124 and is forced into protrusion 138 thereby impacting the primer, discharging the cartridge, and expelling slug 144 from casing 142. Slug 144 is propelled into the intended target. As shaft 104 and firing pin 120 are rarely damaged in use, both shaft 104 and firing pin 120 may be reused with a new cartridge and containment housing repeatedly after recovery.

FIG. 3A shows an alternate embodiment of arrowhead 102. Containment housing 124 further includes retaining tab 160. Retaining tab 160 is an annular wedge shaped projection extending from the interior surface of containment housing 124 into cavity 148. The size of retaining tab 160 is relative to the caliber of cartridge being employed. A larger caliber results in the need for a larger retaining tab. In a preferred embodiment, retaining tab 160 may also be a single projection or a collection of projections spaced in the same plane around the interior circumference. Formed between retaining tab 160 and shoulder 156 is slot 166. Slot 166 is sized to fit base 140 of cartridge 122.

FIG. 3B shows arrowhead 102 as assembled. Cartridge 122 is housed in cavity 158. Base 140 rests in slot 166 adjacent retaining tab 160 and shoulder 156. Slug 144 extends through forward opening 150. Firing pin 120 is threadably engaged with containment housing 124. Threads 154 and threads 136 prevent over insertion of firing pin 120 into cavity 148 resulting in gap 162 between protrusion 138 and base 140. Retaining tab 160 prevents cartridge 122 from sliding backwards and contacting firing pin 120 during flight and to reduce the possibility of accidental discharge should the arrowhead be dropped or knocked against a hard surface. Threads 146 of threaded section 130 engage internal threads 112 to securely attach the arrowhead to shaft 104.

In use, cartridge 122 is loaded into containment housing 124 through rearward opening 152. Cartridge 122 is advanced through cavity 148 and cavity 158 until base 140 passes over retaining tab 160 and abuts shoulder 156. The wedge shape and relative size of retaining tab 160 allows base 140 to pass over retaining tab 160 until base 140 abuts shoulder 156 and rests in slot 166. Firing pin 120 is attached to containment housing 124 such that threads 136 engage threads 154. Firing pin 120 is tightened to containment housing 124. Retaining tab 160 and gap 162 separate protrusion 138 from cartridge 122. Arrowhead 102 is attached to shaft 104 such that threads 146 engage internal threads 112 to complete assembly of arrow 100. Arrow 100 is delivered to an intended target. When arrowhead 102 strikes the intended target, cartridge 122 slides backward through containment housing 124 breaking retaining tab 160. Cartridge 122 contacts protrusion 138 discharging cartridge 122. Slug 144 is propelled from casing 142 and containment housing 124 into the intended target. Shaft 104 may be reused with a freshly assembled ammunition delivery system arrowhead once the used arrowhead is removed.

FIG. 4A shows an alternate embodiment, arrowhead 103. Spring 194 is positioned between firing pin 120 and cartridge 122. Spring 194 may be attached to firing pin 120. In the preferred embodiment, spring 194 is formed from steel and has a spring constant in the range of 20 to 100 N/m, other spring constants will suffice. Also, in a preferred embodiment, the spring takes the form of a frustoconical helical spring. In this embodiment, the spring, when compressed, is thin enough to allow contact of the primer with the protrusion. In general, protrusion 138 is capable of extending through the length of a fully compressed spring 194. In an alternate embodiment, spring 194 is comprised of synthetic foam.

Containment housing 124 further includes threads 164 and window 126. Housing 124 is engaged with cap 170. Threads 164 surround the exterior of containment housing 124 adjacent to forward opening 150. Cap 170 is generally cylindrical and includes an open end, a closed end, and cavity 188. Cap 170 may also include vent 190. Vent 190 is a hole or plurality of radial holes which pass through cap 170 and in to cavity 188. Adjacent the open end are threads 168. Threads 168 are on the interior of cap 170 and are sized to engage threads 164. Cap 170 protects cartridge 122 from accidental discharge should an assembled arrowhead be dropped or knocked against a hard surface. Window 126 is a hole passing through the exterior of containment housing 124 and opening into cavity 158. Window 126 allows a user to visually identify if a cartridge has been loaded in containment housing 124 without removing cap 170. In an alternate embodiment, cap 170 is made of a flexible material such as neoprene and does not include internal threads. In a preferred embodiment, cap 170 is press fit into place over forward opening 150.

FIG. 4B shows arrowhead 103 assembled. Cartridge 122 rests in cavity 158 and base 140 abuts shoulder 156. Slug 144 extends through forward opening 150. Head section 134 of firing pin 120 is threadably engaged with containment housing 124. Threads 154 and threads 136 prevent firing pin 120 from over insertion into cavity 148. As a result, gap 162 exists between protrusion 138 and base 140. Spring 194 biases cartridge 122 away from firing pin 120 to safeguard cartridge 122 from accidently contacting protrusion 138 and discharging the cartridge. Threads 168 of cap 170 engage threads 164 to securely attach cap 170 to containment housing 124. Gap 192 separates cartridge 122 from the interior surface of cap 170. Threads 146 of threaded section 130 engage internal threads 112 to securely attach the arrowhead to shaft 104. In an alternate embodiment, retaining tab 160 may be used in conjunction with a containment housing incorporating cap 170.

In use, cartridge 122 is loaded into containment housing 124 through rearward opening 152. Cartridge 122 is advanced through cavity 148 and through cavity 158 until base 140 abuts shoulder 156. Firing pin 120 is attached to containment housing 124 such that threads 136 engage threads 154 and spring 194 abuts base 140. Firing pin 120 is tightened to containment housing 124 against the bias of spring 194 until protrusion 138 is separated from cartridge 122 by gap 162. Cap 170 is attached to containment housing 124 such that threads 168 engage threads 164. Arrowhead 103 is attached to shaft 104 such that threads 146 engage internal threads 112 to complete assembly of arrow 100. If needed, a user may observe a cartridge through window 126 without removing the cap. In preparation for deployment, cap 170 is removed from containment housing 124. Arrow 100 is deployed. When arrowhead 103 strikes the intended target, cartridge 122 slides backward through containment housing 124 against the bias of spring 194 into protrusion 138 thereby discharging cartridge 122. Slug 144 is propelled into the intended target. Shaft 104 may be reused with another ammunition delivery system arrowhead once the used arrowhead is removed.

In an alternate embodiment, cap 170 is not removed and thus remains engaged with housing 124 during use. Vent 190 allows the escape of ignition gases after the discharging of cartridge 122.

Figure 5C:
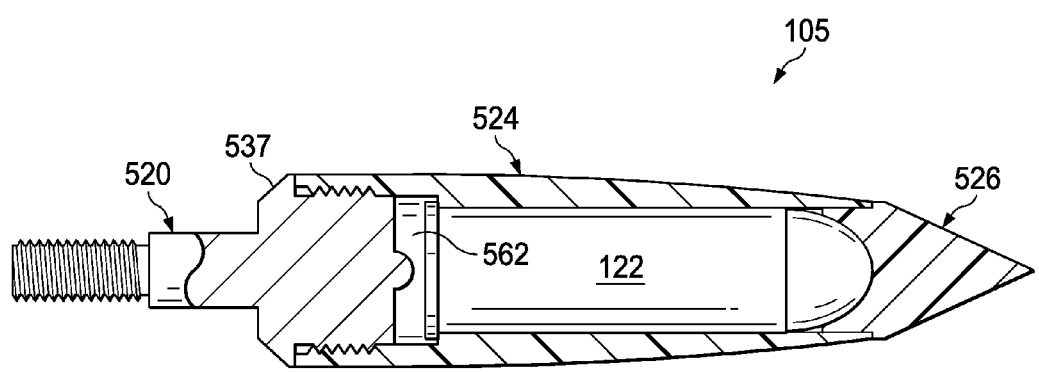
FIG. 5C is an assembled partial cut-away view of an alternate embodiment of an ammunition delivery system arrowhead of this disclosure.
Figure 5B:
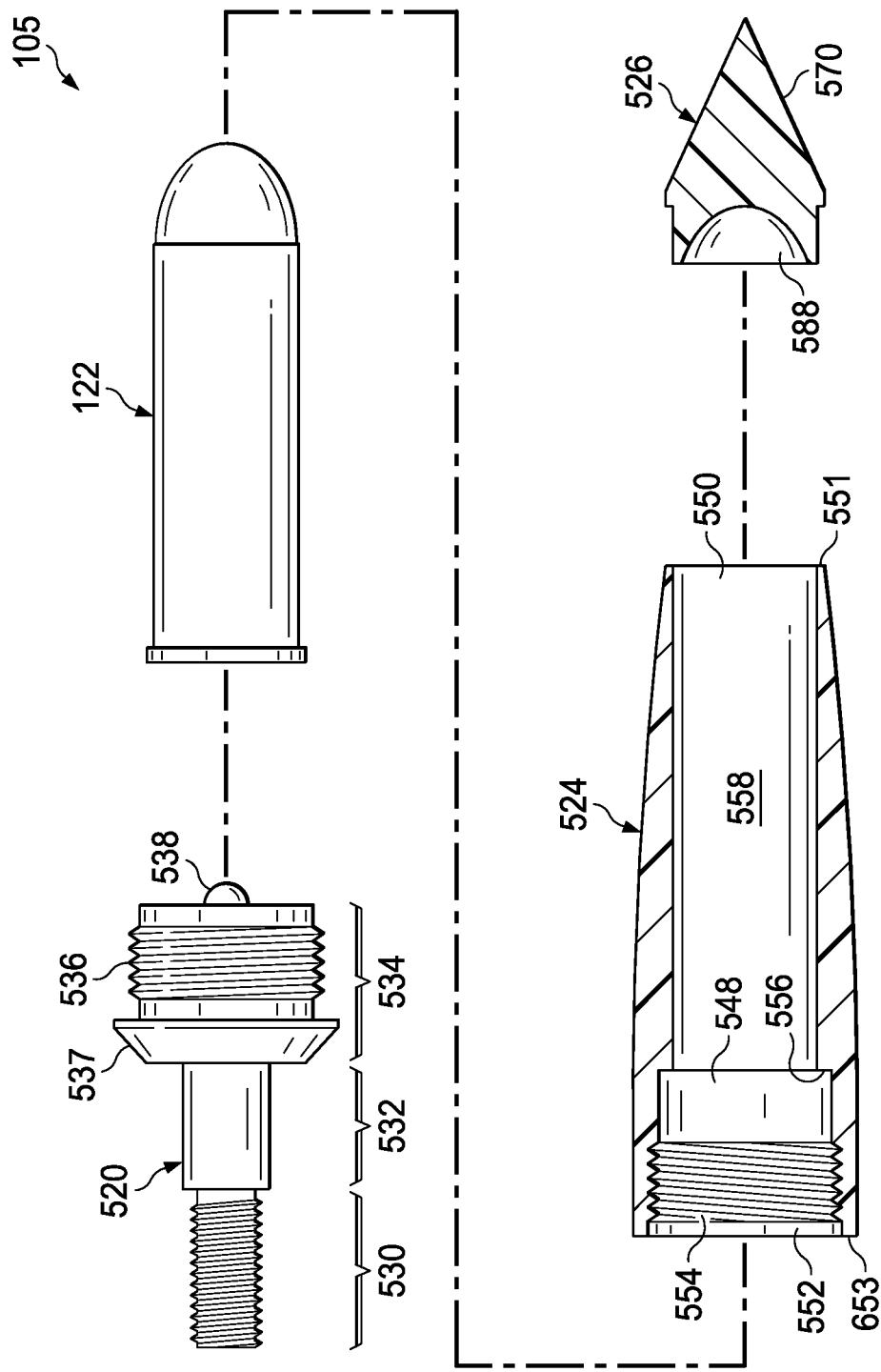
FIG. 5B is an exploded, partial cut-away view of an alternate embodiment of an ammunition delivery system arrowhead of this disclosure.

FIGS. 5A and 5B show an alternate embodiment, arrowhead 105. Arrowhead 105 is comprised of firing pin 520 threadably engaged with housing 524. Cone 526 is pressfit in to housing 524. Cartridge 122 is seated within housing 524.

Firing pin 520 is generally cylindrically shaped and comprised of threaded section 530, middle section 532, and head section 534. All three sections of firing pin 520 are integrally formed and axially aligned. Threaded section 530 includes threads sized to engage threads 112 of shaft 104. Head section 534 includes threads 536. Head section further includes collar 537. Collar 537 has a diameter slightly larger than the diameter of the remainder of head section 534. Protrusion 538 extends from head section 534 and is generally concentrically aligned with the longitudinal axis of firing pin 520. Firing pin 520 is preferably manufactured of aluminum, steel, or rigid molded plastic.

Housing 524 is generally a hollow cylinder having rearward opening 552 at end 553 and forward opening 550 at end 551. End 553 has a slightly larger diameter than end end 551 thus the exterior of containment housing 524 tapers through its length from end 553 to end 551. The interior of housing 524 includes a cylindrically shaped cavity 558 adjacent a second concentrically aligned and cylindrically shaped cavity 548. Shoulder 556 separates cavity 548 from cavity 558. Rearward opening 552 is sized to accommodate head section 534 of firing pin 520. Rearward opening 552 opens to cavity 548. Cavity 548 includes threads 554 which engage threads 536. Forward opening 550 opens to cavity 558. Housing 524 is preferably manufactured of molded plastic, transparent acrylic resin, or polypropylene. Cone 526 is made of lubricated nylon material and includes a pointed nose 570 and a generally dome shaped cavity 588.

As shown in FIG. 5C, as assembled, cartridge 122 rests in cavity 558 and base 140 abuts shoulder 556. Head section of firing pin 520 is threadably engaged with housing 524. Firing pin 520 is advanced into cavity 548 until collar 537 abuts end 553. As a result, gap 562 exists between protrusion 538 and base 140 of cartridge 122. Cone 526 is frictionally engaged with housing 524 in forward opening 550 but adhesive may also be used. Cavity 588 surrounds slug 144. Threaded section 530 engages threads 112 to attach arrowhead 105 to shaft 104. In an alternate embodiment, spring 194 may be positioned between firing pin 520 and cartridge 122. Spring 194 may be attached to firing pin 520.

In use, cartridge 122 is inserted into housing 524 through rearward opening 552. Cartridge 122 is advanced through cavity 548 and through cavity 558 until base 140 abuts shoulder 556. Firing pin 520 is threadably attached to housing 524. Firing pin 520 is tightened to housing 524 until collar 537 abuts end 553. Gap 162 is formed between protrusion 138 and cartridge 122. Cone 526 is press fit in to forward opening 550. Arrowhead 105 is threadably attached to shaft 104.

Cone 526 is preferably left in place during use. Pointed nose 570 provides aerodynamic advantages and imparts deeper penetration into an intended target over blunt shaped cartridges. As arrowhead 105 strikes the intended target, cone 526 shatters and cartridge 122 slides backward through housing 524 into protrusion 538. Cartridge 122 is discharged and slug 144 is propelled into the intended target. Shaft 104 and firing pin 520 may be reused with a new housing, cartridge, and nose.

Figure 6A:
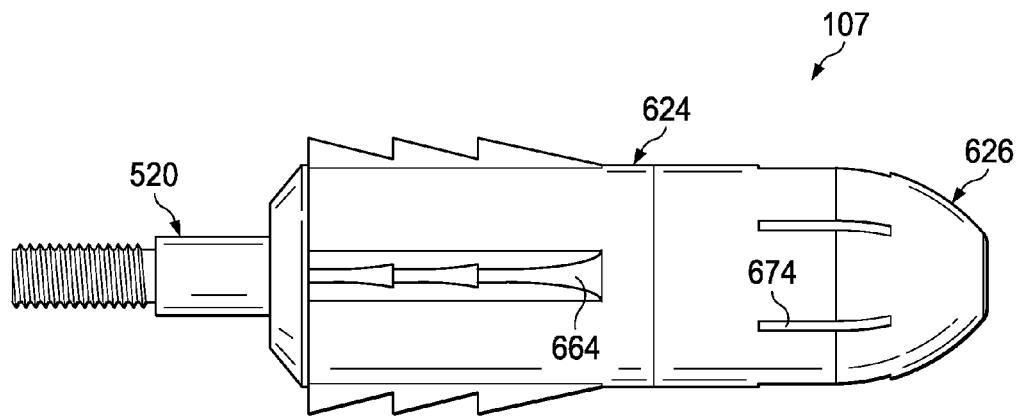
FIG. 6A is an elevation view of an alternate embodiment of an ammunition delivery system arrowhead of this disclosure.
Figure 6C:
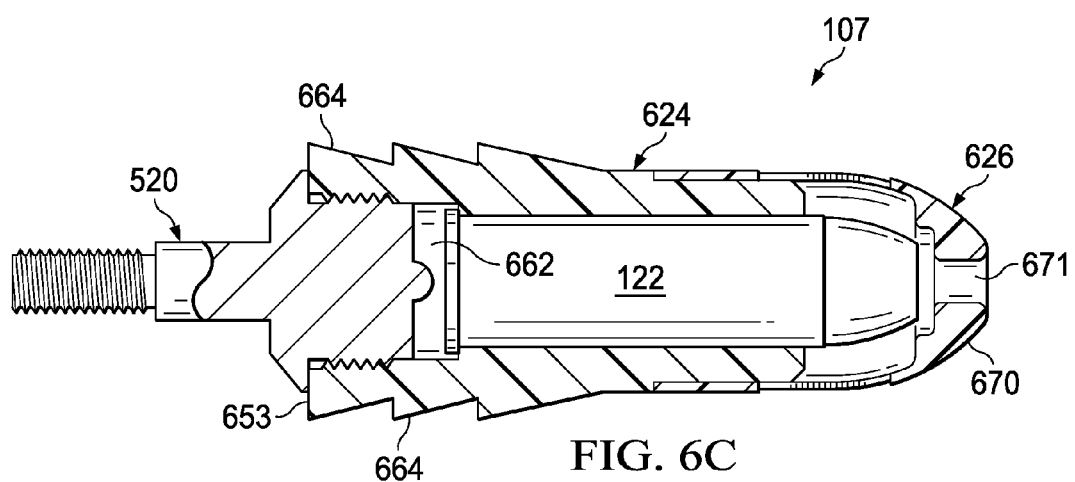
FIG. 6C is an assembled partial cut-away view of an alternate embodiment of an ammunition delivery system arrowhead of this disclosure.
Figure 6B:
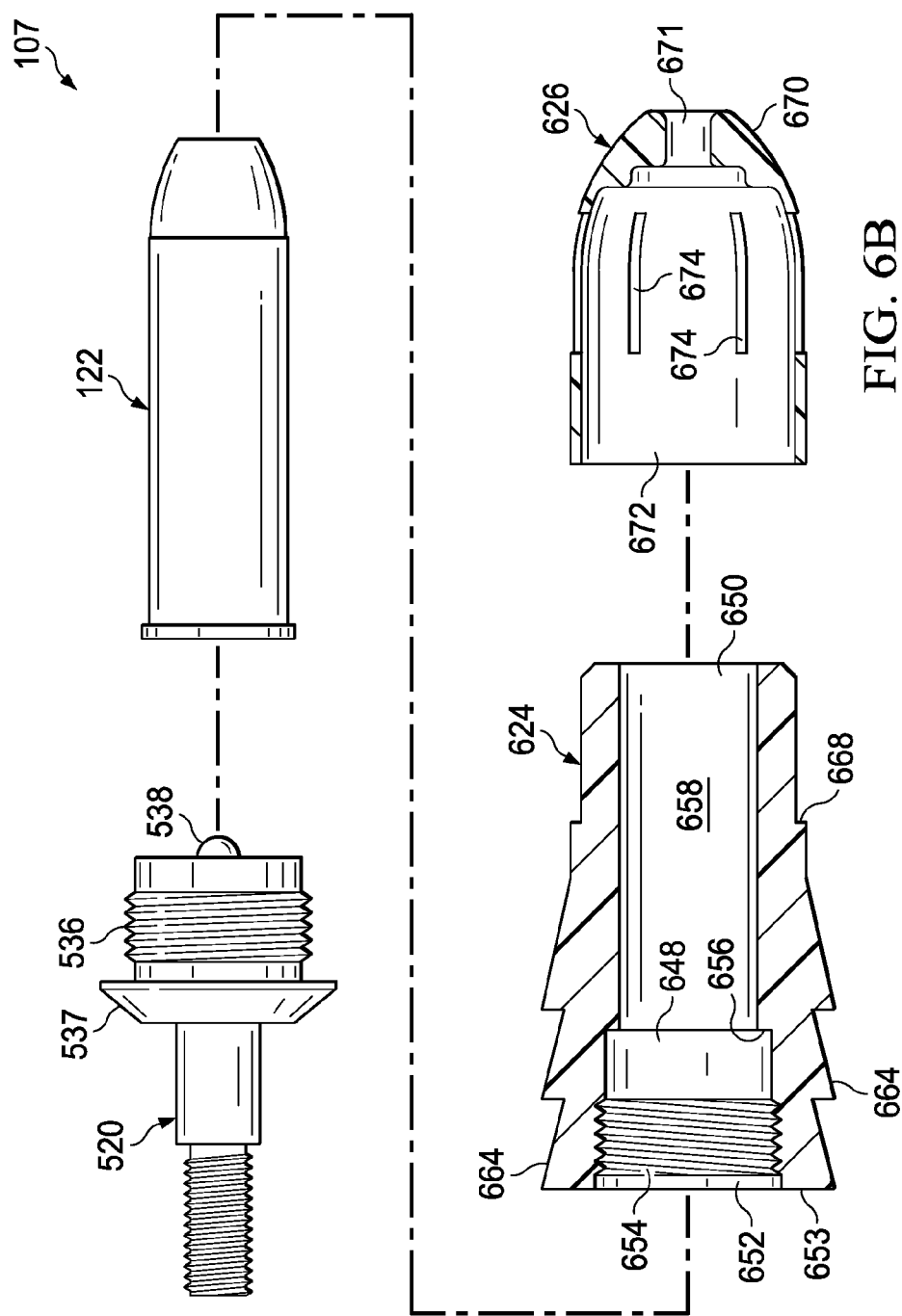
FIG. 6B is an exploded, partial cut-away view of an alternate embodiment of an ammunition delivery system arrowhead of this disclosure.

FIGS. 6A and 6B show an alternate embodiment, arrowhead 107. Arrowhead 107 is comprised of firing pin 520 threadably engaged with housing 624. Cap 626 is pressfit onto housing 624. Cartridge 122 is seated within housing 624.

Housing 624 is generally a hollow cylinder having rearward opening 652 at end 653 and forward opening 650 on the opposite end. Housing 624 includes a cylindrically shaped cavity 658 adjacent a second concentrically aligned and cylindrically shaped cavity 648. Shoulder 656 is adjacent both and separates cavity 648 from cavity 658. Rearward opening 652 opens to cavity 648. Cavity 648 includes threads 654 which engage threads 536. Forward opening 650 opens to cavity 658. The exterior of housing 624 includes shoulder 668. Housing 624 includes vanes 664. Vanes 664 are generally triangular shaped and are integrally formed with housing 624. As shown, vanes 664 comprise four equidistantly spaced groups of three longitudinally aligned vanes extending from housing 624 at end 653. It is envisioned that more or fewer vanes in a group and more or fewer groupings of vanes is possible. The total number of vanes and the configuration of the vanes around housing 624 can be adjusted according to intended use or cartridge size. Vanes 664 provide aerodynamic advantages which help stabilize the arrowhead during use. Cap 626 is generally a hollow cylinder and includes a forward end 670 and an open end 672. Forward end 670 includes hole 671. Cap 626 includes a plurality of equidistantly spaced slits 674.

As shown in FIG. 6C, when assembled, cartridge 122 rests in cavity 658 and base 140 abuts shoulder 656. Head section of firing pin 520 is threadably engaged with housing 624. Firing pin 520 is advanced into cavity 648 until collar 537 abuts end 653. As a result, gap 662 exists between protrusion 538 and base 140. Cap 626 is frictionally engaged with housing 624 and advanced over forward opening 650 until cap 626 abuts shoulder 668. Threaded section 530 engages threads 112 to attach arrowhead 107 to shaft 104. In an alternate embodiment, spring 194 may be positioned between firing pin 520 and cartridge 122 and spring 194 may be attached to firing pin 520 with adhesive or other common in the art methods.

In use, cartridge 122 is inserted into housing 624 through rearward opening 652. Cartridge 122 is advanced through cavity 648 and through cavity 658 until base 140 abuts shoulder 656. Firing pin 520 is threadably attached to housing 624 at end 653. Firing pin 520 is tightened to housing 624 until collar 537 abuts end 553 and thus gap 662 is maintained between protrusion 138 and cartridge 122. Cap 626 is press fit over forward opening 550. Arrowhead 105 is threadably attached to shaft 104.

Cap 626 remains engaged with housing 624 during use. As arrowhead 107 strikes the intended target, cap 626 shatters and cartridge 122 slides backward through housing 624 into protrusion 538. Cartridge 122 is discharged and slug 144 is propelled into the intended target. Slits 674 and hole 671 allow the escape of ignition gases after the discharging of cartridge 122. Slits 674 also function as a flash suppressor diverting the discharge flare to radial angles away from the axis of travel. Shaft 104 and firing pin 520 may be reused with a new housing, cartridge, and nose.

Figure 7A:
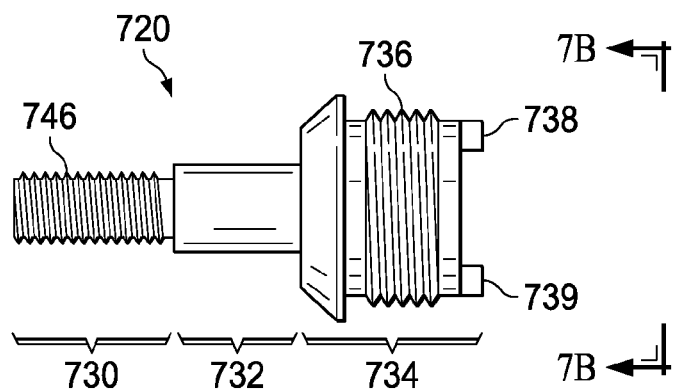
FIG. 7A is an elevation view of an alternate embodiment of a firing pin of the ammunition delivery system arrowhead of this disclosure.
Figure 7B:
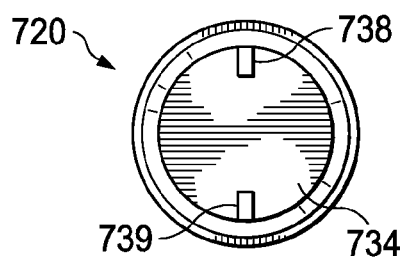
FIG. 7B is an end view of an alternate embodiment of a firing pin of the ammunition delivery system arrowhead of this disclosure.

FIGS. 7A and 7B show an alternate embodiment of a firing pin. Firing pin 720 is comprised of threaded section 730, middle section 732, and head section 734. Threaded section 730 includes threads 746 sized to engage threads 112 of shaft 104. Threaded section 730 is integrally formed with middle section 732. Middle section 732 is cylindrically shaped and typically has a diameter generally equal to the diameter of shaft 104. Head section 734 is integrally formed with middle section 732 and further includes threads 736. Protrusions 738 and 739 extend from head section 734. Protrusions 738 and 739 are generally located near the perimeter of head section 734. Protrusions 738 and 739 are offset from the longitudinal central axis of firing pin 720 in order to operate with a rimfire cartridge. The offset protrusions are not limited to two. Firing pin 720 is preferably manufactured of aluminum, steel, or rigid molded plastic. Firing pin 720 can be used with any of the previously described arrowhead configurations.

Figure 8:
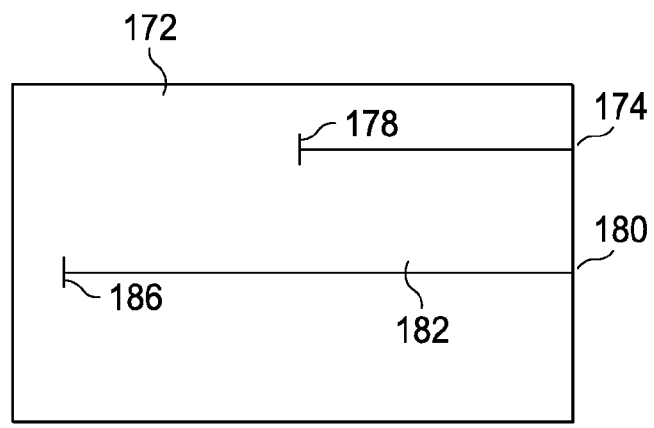
FIG. 8 is a test comparison of the penetration depths of a preferred embodiment of an ammunition delivery system arrowhead of this disclosure versus an arrow having a standard arrowhead.

FIG. 8 shows the test results of an ammunition delivery system arrowhead of the present disclosure discharged into ballistics test medium 172. Ballistics test medium 172 is a twenty inch block of PERMA-GEL™ synthetic "soft tissue" medium. PERMA-GEL™ is used for the testing and comparison of different types of projectiles and loads and can be found at www.perma-gel.com. The bow used in the test was a 62 pound pressure bow at a distance of twenty yards. A conventional arrowhead, fired from the same bow, entered ballistics test medium 172 at point 174 and stopped at point 178. The conventional arrowhead traveled approximately 8.3 inches through ballistics test medium 172. An ammunition delivery system arrowhead as disclosed herein entered ballistics test medium at point 180. At point 182, approximately 4.2 inches into ballistics test medium 172, the cartridge housed in the ammunition delivery system arrowhead was discharged. The discharged slug continued to point 186 penetrating an additional approximate twelve inches for a total penetration of approximately 16.3 inches.

It will be appreciated by those skilled in the art that changes could be made to the embodiments described above without departing from the broad inventive concept. It is understood, therefore, that this invention is not limited to the particular embodiments disclosed, but it is intended to cover modifications within the spirit and scope of the present invention as defined by the appended claims.

The invention claimed is:

1. An ammunition delivery system for delivering an ammunition cartridge comprising:
a firing pin comprising a head section and a protrusion extending from the head section;
a housing removably connected to the head section;
the housing comprising a generally hollow cylinder and a first interior chamber separated from a second interior chamber by a shoulder;
a forward opening leading to the second interior chamber;
a cap engaged with the housing and covering the forward opening;
wherein the second interior chamber is slidably engaged with the ammunition cartridge and the shoulder contacts the ammunition cartridge; and,
wherein a gap is defined within the first interior chamber between the protrusion and the ammunition cartridge.

2. The ammunition delivery system of claim 1 further comprising:
an exterior shoulder on the housing;
a set of vanes extending from the housing; and
wherein the cap abuts the exterior shoulder and further comprises a plurality of slits.

3. The system of claim 1 wherein the cap is a pointed nosecone adjacent the second interior chamber and further comprises a cavity adjacent the ammunition cartridge.

4. The ammunition delivery system of claim 2 where the protrusion is concentrically aligned with the longitudinal axis of the firing pin.

5. An ammunition delivery system for delivering an ammunition cartridge comprising:
a firing pin comprising a head section and a protrusion extending from the head section;
a housing removably connected to the head section;
the housing comprising a generally hollow cylinder and a first interior chamber separated from a second interior chamber by a shoulder;
wherein the second interior chamber is slidably engaged with the ammunition cartridge and the shoulder contacts the ammunition cartridge;
wherein a gap is defined within the first interior chamber between the protrusion and the ammunition cartridge; and,
where the head section comprises a set of protrusions and each protrusion of the set of protrusions is offset from the longitudinal axis of the firing pin.

6. An ammunition delivery system for delivering an ammunition cartridge comprising:
a firing pin comprising a head section and a protrusion extending from the head section;
a housing removably connected to the head section;
the housing comprising a generally hollow cylinder and a first interior chamber separated from a second interior chamber by a shoulder;
an annular retaining tab extending into the first interior chamber;
wherein the second interior chamber is slidably engaged with the ammunition cartridge and the shoulder contacts the ammunition cartridge; and,
wherein a gap is defined within the first interior chamber between the protrusion and the ammunition cartridge.

7. An ammunition delivery system for delivering an ammunition cartridge comprising:
a firing pin comprising a head section and a protrusion extending from the head section;
a housing removably connected to the head section;
the housing comprising a generally hollow cylinder and a first interior chamber separated from a second interior chamber by a shoulder;
a spring adjacent the head section and adjacent the ammunition cartridge;

wherein the second interior chamber is slidably engaged with the ammunition cartridge and the shoulder contacts the ammunition cartridge; and, wherein a gap is defined within the first interior chamber between the protrusion and the ammunition cartridge.

8. An ammunition delivery system for delivering an ammunition cartridge comprising:
   a firing pin comprising a head section and a protrusion extending from the head section;
   a housing removably connected to the head section;
   the housing comprising a generally hollow cylinder and a first interior chamber separated from a second interior chamber by a shoulder;
   wherein the second interior chamber is slidably engaged with the ammunition cartridge and the shoulder contacts the ammunition cartridge;
   wherein a gap is defined within the first interior chamber between the protrusion and the ammunition cartridge; and,
   wherein the head section further comprises a collar and the collar abuts the housing.

9. An arrowhead attached to an arrow shaft for delivering a round of ammunition, the arrowhead comprising:
   a generally cylindrical hollow housing comprising a first opening leading to a first cavity and a second opening leading to a second cavity where the first cavity and the second cavity are separated by an internal shoulder;
   a generally cylindrical firing pin threadably engaged with the arrow shaft and threadably engaged with the first cavity;
   a protrusion extending from the firing pin into the first cavity;
   a nosepiece engaged with the housing and covering the second opening; and,
   wherein the second cavity is slidably engaged with the round of ammunition and the internal shoulder contacts the round of ammunition.

10. The arrowhead of claim 9 where the protrusion is concentrically aligned with the longitudinal axis of the firing pin.

11. The arrowhead of claim 9 where the protrusion is offset from the longitudinal axis of the firing pin.

12. The arrowhead of claim 9 further comprising a spring adjacent the firing pin and adjacent the round of ammunition.

13. The arrowhead of claim 9 where the firing pin further comprises a collar and the collar abuts the housing at the first opening.

14. The arrowhead of claim 9 where the nosecone further comprises a pointed end and a cavity where the cavity is adjacent the round of ammunition.

15. The arrowhead of claim 9 where the nosecone comprises a plurality of slits and abuts an exterior shoulder.

16. A method for delivering ammunition via an arrow comprising the steps of:
   providing a firing pin with a protrusion;
   providing a containment housing comprising a rearward opening leading to a first cavity and a forward opening leading to a second cavity where the first cavity and the second cavity are separated by a shoulder;
   inserting the ammunition through the rearward opening;
   seating the ammunition in the second cavity;
   abutting the ammunition against the shoulder;
   attaching the firing pin to the containment housing;
   providing a gap between the protrusion and the ammunition;
   covering the forward opening with a cap engaged with the containment housing; and,
   attaching the firing pin to the arrow.

17. The method of claim 16 further comprising:
   biasing the ammunition away from the firing pin with a spring.

18. The method of claim 16 further comprising:
   providing a set of vanes extending from the housing.

19. The method of claim 16 further comprising:
   providing a firing pin with an offset protrusion.

* * * * *